United States Patent
Schroeder et al.

(10) Patent No.: US 11,721,430 B1
(45) Date of Patent: Aug. 8, 2023

(54) METHODS, SYSTEMS, AND COMPUTER READABLE MEDIA FOR USING MACHINE LEARNING IN DETECTING DRUG DIVERSION

(71) Applicant: Duke University, Durham, NC (US)

(72) Inventors: Rebecca Ann Schroeder, Durham, NC (US); Nigel Benjamin Neely, Durham, NC (US); Timothy William Dunn, Durham, NC (US); Evan S. Frasure, III, Cary, NC (US); Erich Senin Huang, Durham, NC (US); Joseph Puthenveetil Mathew, Durham, NC (US)

(73) Assignee: Duke University, Durham, NC (US)

( * ) Notice: Subject to any disclaimer, the term of this patent is extended or adjusted under 35 U.S.C. 154(b) by 210 days.

(21) Appl. No.: 17/072,975

(22) Filed: Oct. 16, 2020

Related U.S. Application Data

(60) Provisional application No. 62/916,536, filed on Oct. 17, 2019.

(51) Int. Cl.
*G16H 40/20* (2018.01)
*G16H 20/13* (2018.01)
(Continued)

(52) U.S. Cl.
CPC ............ *G16H 40/20* (2018.01); *G06N 20/20* (2019.01); *G06Q 10/06398* (2013.01);
(Continued)

(58) Field of Classification Search
None
See application file for complete search history.

(56) References Cited

U.S. PATENT DOCUMENTS 6,842,736 B1 1/2005 Brzozowski
8,606,596 B1 * 12/2013 Bochenko .............. G06Q 10/00
705/2

(Continued)

OTHER PUBLICATIONS

Anesthesia Patient Safety Foundation (APSF), Large Anesthesia/Practice Management Groups: Drug Diversion in the Anesthesia profession: how can APSF help everyone be safe? Supplemental Digital Content, http://links.lww.com/AA/C616. (4 pages) (2017).

(Continued)

*Primary Examiner* — John A Pauls
(74) *Attorney, Agent, or Firm* — Jenkins, Wilson, Taylor & Hunt, P.A.

(57) ABSTRACT

According to one method for using machine learning in detecting drug diversion, the method comprises receiving, as input, an observed drug dispensation amount associated with a drug dispensation event related to a drug provider along with other drug dispensation event data, wherein the drug dispensation event data comprises drug provider information, procedure information, and patient information; generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm and is trained using one or more data sets associated with related drug dispensation events; and outputting, by the drug diversion detection algorithm, information indicating that the observed drug dispensation amount is aberrant.

20 Claims, 14 Drawing Sheets
(9 of 14 Drawing Sheet(s) Filed in Color)

(51) Int. Cl.

| | |
|---|---|
| *G16H 50/20* | (2018.01) |
| *G16H 70/20* | (2018.01) |
| *G16H 10/60* | (2018.01) |
| *G16H 50/70* | (2018.01) |
| *G06Q 10/105* | (2023.01) |
| *G06Q 10/0639* | (2023.01) |
| *G06N 20/20* | (2019.01) |
| *G16H 70/40* | (2018.01) |
| *A61J 7/00* | (2006.01) |

(52) U.S. Cl.
CPC .......... *G06Q 10/105* (2013.01); *G16H 10/60* (2018.01); *G16H 20/13* (2018.01); *G16H 50/20* (2018.01); *G16H 50/70* (2018.01); *G16H 70/20* (2018.01); *G16H 70/40* (2018.01); *A61J 7/0076* (2013.01)

(56) References Cited

U.S. PATENT DOCUMENTS

| | | | | |
|---|---|---|---|---|
| 2006/0040406 | A1* | 2/2006 | Schneider | G16H 10/40 |
| | | | | 436/514 |
| 2015/0170306 | A1 | 6/2015 | Harper | |
| 2017/0109497 | A1* | 4/2017 | Tribble | G16H 70/40 |
| 2018/0039736 | A1 | 2/2018 | Williams | |
| 2018/0247703 | A1* | 8/2018 | D'Amato | G16H 15/00 |
| 2018/0286505 | A1* | 10/2018 | Kirkendall | G16H 20/10 |
| 2019/0244699 | A1* | 8/2019 | Loebig | G06N 20/20 |
| 2019/0355461 | A1 | 11/2019 | Kumar et al. | |

OTHER PUBLICATIONS

Pelt et al., "Drug Diversion in the Anesthesia Profession: How Can Anesthesia Patient Safety Foundation Help Everyone Be Safe? Report of a Meeting Sponsored by the Anesthesia Patient Safety Foundation," ANAA J. (5 pages) (2019).
BCC Research abstract of "Pharmacy Automation: Technologies and Global Markets," BCC Publishing, retrieved online May 25, 2022, 5 pages (2019).
Becker et al., "Prescription drug misuse: Epidemiology, prevention, identification, and management," UpToDate article (21 pages) (2021).
Booth et al., "Substance abuse among physicians: a survey of academic anesthesiology programs," Anesth Analg., vol. 95, pp. 1024-1030 (2002).
Brenn et al., "Development of a computerized monitoring program to identify narcotic diversion in a pediatric anesthesia practice," Am J Health-Syst Pharm., vol. 72, pp. 1365-1372 (2015).
Bryson et al., "Addiction and substance abuse in anesthesiology," Anesthesiology, vol. 109, No. 5, pp. 905-917 (2008).
Centers for Disease Control and Prevention, "Drug Diversion," Page last reviewed: Nov. 26, 2019. Accessed from: https://www.cdc.gov/injectionsafety/drugdiversion/index.html (4 pages).
Dexter, "Detecting diversion of anesthetic drugs by providers," Anesth Analg., vol. 105, pp. 897-898 (2007).
Epstein et al., "Development of a scheduled drug diversion surveillance system based on an analysis of atypical drug transactions," Anesth Analg., vol. 105, pp. 1053-1060 (2007).
Fan et al., "Diversion of Controlled Drugs in Hospitals: A Scoping Review of Contributors and Safeguards," J. Hosp. Med., vol. 14(7), pp. 419-428 (2019).
HelioMetrics—Healthcare Rx Drug and Pharmacy Diversion, 3 pages, retrieved online Apr. 8, 2022: https://heliometrics.net/.
Invistics Healthcare Solutions, 7 pages, retrieved online Apr. 8, 2022: https://invistics.com/flowlytics-overview/for-healthcare/.
Kitcheck, "Bluesight for Controlled Substances," 6 pages, retrieved online Apr. 8, 2022: https://kitcheck.com/bluesight/controlled-substances/.
BD Healthsight Diversion Management, product website, 5 pages, retrieved online Apr. 8, 2022: https://www.bd.com/en-us/offerings/capabilities/medication-and-supply-management/medication-and-supply-management-software/bd-healthsight-diversion-management.
"Genesis Analytics," Medacist, 5 pages, retrieved online Apr. 8, 2022: https://www.medacist.com/product/genesis-analytics/.
Medacist, "What's Next Changes Everything," 8 pages, retrieved online Apr. 8, 2022: https://www.medacist.com/.
"RxAuditor Analytics," Medacist, 5 pages, retrieved online Apr. 8, 2022: https://www.medacist.com/product/rxauditor-analytics/.
"Scriptrac Analytics," Medacist, 5 pages, retrieved online Apr. 8, 2022: https://www.medacist.com/product/scriptrac-analytics/.
Omnicell Analytics, "Omnicell Analytics for Efficient Drug Diversion Detection," Omnicell products page retrieved online May 25, 2022, 8 pages (2022).
Omnicell Analytics, "Omnicell Analytics," Omnicell product flyer, retrieved online May 25, 2022, 2 pages (2020).
Protenus, "Detect clinical drug diversion," 3 pages, Feb. 1, 2020, retrieved online Apr. 8, 2022: https://www.protenus.com/features/detect-clinical-drug-diversion.
Radars System Programs, 4 pages, retrieved online Apr. 8, 2022: https://www.radars.org/.
Kristof, "Methods, Trends, and Solutions for Drug Diversion." International Association for Healthcare Security and Safety Foundation. IAHSS-F RS-18-01 (2018).
Silverstein et al., "Opioid addiction in anesthesiology." Anesthesiology, vol. 79, pp. 354-375 (1993).
Smyth, "Clustering sequences with hidden Markov models," Advances in Neural Information Processing Systems, pp. 649-654 (1997).
Tate et al., "Drug Diversion Monitoring 2019: An Early Look at Emerging vs. Established Technology." KLAS report (2019). Accessed from: https://klasresearch.com/report/drug-diversionmonitoring-2019/1570.
Van Pelt et al., "Drug Diversion in the Anesthesia Profession: How Can the Anesthesia Patient Safety Foundation Help Everyone Be Safe?" APSF Newsletter, vol. 33, pp. 92-94 (2019).
Warner et al., "Substance use disorder among anesthesiology residents, 1975-2009." JAMA, vol. 310, pp. 2289-2296 (2013).
Wood, "Drug diversion." Aust Prescr., vol. 38(5), pp. 164-166 (2015).

\* cited by examiner

FIG. 5B

METHODS, SYSTEMS, AND COMPUTER READABLE MEDIA FOR USING MACHINE LEARNING IN DETECTING DRUG DIVERSION

CROSS REFERENCE TO RELATED APPLICATIONS

This application claims the benefit of U.S. Provisional Patent Application Ser. No. 62/916,536, filed Oct. 17, 2019, the disclosure of which is incorporated herein by reference in its entirety.

TECHNICAL FIELD

The subject matter described herein relates generally to machine learning algorithms. More particularly, the subject matter described herein includes methods, systems, and computer readable media for using machine learning in detecting drug diversion.

BACKGROUND

Illegal distribution or use of prescription medications (i.e., drug diversion) by drug providers is a problem of great concern in health care. For some drug providers, access to controlled substances can be difficult to resist, leading to risks for the diverters, their patients, and their institutions. Despite efforts to mitigate these risks, including education, complete process redesign of systems for issuing controlled medications for intraoperative use, and electronic tracking of controlled drugs, there continue to be significant problems with abuse, addiction, and even mortality.

There have been efforts to use pharmacy information management systems (PIMS) to identify patterns consistent with an elevated risk of diversion of controlled substance for personal or alternate use. These surveillance methods often consist of auditing an electronic medication dispensing system (MDS). However, these systems have drawbacks, such as the need for significant user interpretation. Additionally, some job categories in a hospital setting are not easily monitored. For example, monitoring drug diversion in anesthesiology trainees, who continually rotate with no stable practice pattern, is especially problematic. Supervisors and trainee program directors are responsible for reviewing the reports and determining if they contain any issues of concern. These can be complex reports. Residents rotate to different clinical services each month, dramatically different types and amount of narcotics are administered, and anesthesia technique and practice style can have a significant impact on the amount of narcotics used during any surgical procedure. In addition, because so many patients now take long-acting opioids, this complicates their management, with the consequence that these patients require greater intraoperative supplementation in a way not evident from simply reviewing procedure codes. Detecting an individual who is diverting drugs away from patient care against significant background variability is extremely difficult for the human mind to ascertain. Hence, there is a need for robust drug diversion monitoring systems that account for a variety of workflow scenarios.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The subject matter described herein includes methods, systems, and computer readable media for using machine learning in detecting drug diversion. A method for using machine learning in detecting drug diversion, the method comprising: receiving, as input, an observed drug dispensation amount associated with a drug dispensation event related to a drug provider along with other drug dispensation event data, wherein the drug dispensation event data comprises drug provider information, procedure information, and patient information; generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm and is trained using one or more data sets associated with related drug dispensation events; and outputting, by the drug diversion detection algorithm, information indicating that the observed drug dispensation amount is aberrant.

A system for using machine learning in detecting drug diversion, the system comprising a computing platform including at least one processor and memory. The computing platform is configured for: receiving, as input, an observed drug dispensation amount associated with a drug dispensation event related to a drug provider along with other drug dispensation event data, wherein the drug dispensation event data comprises drug provider information, procedure information, and patient information; generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm and is trained using one or more data sets associated with related drug dispensation events; and outputting, by the drug diversion detection algorithm, information indicating that the observed drug dispensation amount is aberrant.

The subject matter described herein may be implemented in software in combination with hardware and/or firmware. For example, the subject matter described herein may be implemented in software executed by a processor (e.g., a hardware-based processor). In one example implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, such as field programmable gate arrays, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter described herein will now be explained with reference to the accompanying drawings of which:

FIGS. 5A-5D depict charts from a screenshot of an example drug diversion dashboard;

DETAILED DESCRIPTION

Figure 1:
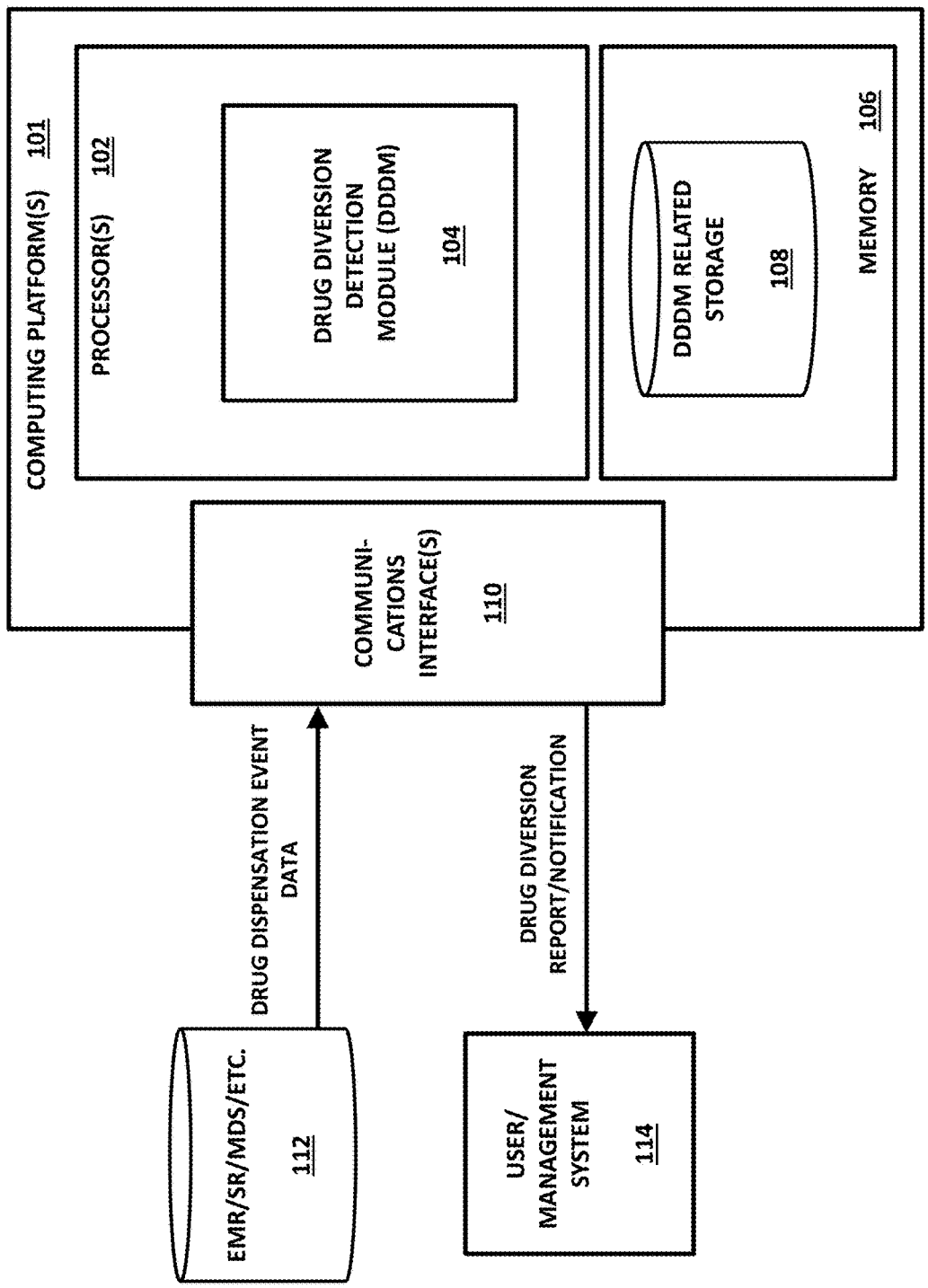
FIG. 1 is a diagram illustrating an example system for using machine learning in detecting drug diversion.

The subject matter described herein discloses methods, systems, and computer readable media for using machine learning in detecting drug diversion. For example, a drug diversion detection system in accordance with some aspects described herein may obtain drug dispensation event data from disparate sources (e.g., an electronic medical record (EMR) system and a medication dispensing system (MDS)) and may analyze the drug dispensation event data to expose or detect anomalous or aberrant behavior. In this example, analyzing anomalous or aberrant behavior may involve a trained machine learning based algorithm that determines expected drug dispensation amounts for particular procedures or treatments and determines if significant differences between the expected drug dispensation amounts and the observed (e.g., recorded) dispensation amounts exist (e.g., if a residual amount (observed—expected) is higher than a predetermined threshold value or if an observed amount is two standard deviations or higher than an expected amount).

By providing techniques, mechanisms, and/or methods for using machine learning in detecting potential drug diversion, drug diversion detection can be performed more efficiently. Moreover, by using machine learning based tools to detect possible drug diversion, drug diversion can be reduced and related consequences can be mitigated, such as by identifying drug providers that need appropriate intervention for drug abuse, improve quality of care for patients, and reducing healthcare costs.

As used herein, the term "node" refers to a physical computing platform including one or more processors and memory.

As used herein, the terms "function" or "module" refer to software in combination with hardware and/or firmware for implementing features described herein. In some embodiments, a module may include a field-programmable gate array (FPGA), an application-specific integrated circuit (ASIC), or a processor.

Articles "a" and "an" are used herein to refer to one or to more than one (i.e. at least one) of the grammatical object of the article. By way of example, "an element" means at least one element and can include more than one element.

As used herein, the term "and/or" when used in the context of a list of entities, refers to the entities being present singly or in any and every possible combination and sub-combination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or"). As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder, or condition.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the patient comprises a human.

As used herein, the term "drug" generally refers to controlled substances, such as prescription medications, that are administered in a hospital, clinical, or pharmacy setting. Of particular interest are medications that are frequently targeted for illegal personal use or for financial gain. Some examples of these frequently targeted medications include opioids and benzodiazepines.

Unless otherwise defined, all technical terms used herein have the same meaning as commonly understood by one of ordinary skill in the art to which this disclosure belongs.

FIG. 1 is a diagram illustrating an example drug diversion detection system (DDDS) 100 for using machine learning in detecting drug diversion. DDDS 100 may include any suitable entity (e.g., a mobile device, a computer, or multiple servers) configurable for detecting drug diversion and/or related aspects using a trained machine learning based model or algorithm. For example, DDDS 100 may include a memory and at least one processor for executing a module (e.g., an application or software) that uses machine learning in detecting drug diversion.

In some embodiments, DDDS 100 and/or a related machine learning algorithm may use drug dispensation event data as input and may output various types of information for monitoring and/or detecting drug diversion. For example, DDDS 100 and/or a related machine learning algorithm may use drug dispensation event data to determine or predict an appropriate or expected drug dispensation amount for a given drug dispensation event, to determine whether an observed drug dispensation amount is aberrant, to generate drug dispensation patterns for one or more drug providers, to detect whether a drug dispensation pattern is consistent with (e.g., indicates or appears to indicate) drug diversion, and/or to classify drug dispensation patterns associated with drug providers into different drug dispensation groups.

Referring to FIG. 1, DDDS 100 may include one or more computing platform(s) 101. Computing platform(s) 101 may include processor(s) 102. Processor(s) 102 may represent any suitable entity or entities (e.g., one or more hardware-based processor) for processing information and executing instructions or operations. Each of processor(s) 102 may be any type of processor, such as a central processor unit (CPU), a microprocessor, a multi-core processor, and the like. Computing platform(s) 101 may further include a memory 106 for storing information and instructions to be executed by processor(s) 102. In some embodiments, memory 106 can comprise one or more of random access memory (RAM), read only memory (ROM), static storage such as a magnetic or optical disk, or any other type of machine or non-transitory computer-readable medium.

Computing platform(s) 101 may further include one or more communications interface(s) 110, such as a network interface card or a communications device, configured to provide communications access to various entities (e.g., network-connected devices). In some embodiments, communications interface(s) 110 may allow interaction between DDDS 100 or related entities and various data sources 112. Each of data sources 112 may represent one or more suitable entities (e.g., a database, a data management system, and/or data storage devices) containing various types of data usable by DDDS 100 or related entities. For example, data sources 112 may include an electronic medical record (EMR) system (e.g., EPIC®), a medication dispensing system (MDS) (e.g., Omnicell®), a scheduling records (SR) system, and/or other sources or systems. Data obtained or compiled from data sources 112 may generally be referred to herein as data dispensation event data, which may comprise drug provider information, procedure information, and/or patient information.

In some embodiments, data sources 112 may represent disparate medical systems that generate and/or contain drug dispensation event data or portions thereof may not communicate or may not communicate easily with one another and/or with DDDS 100 or DDDM 104. For example, an EMR system may include patient information, an MDS system may include drug information, and an scheduling records (SR) system may include drug provider information or other workplace information relevant to drug dispensation, e.g., job role, work schedule, clinical assignments, and attendance record. In this example, communications interface(s) 110 and/or related APIs and logic may be utilized for accessing or collecting data from these data sources 112.

In some embodiments, communications interface(s) 110 may allow interaction between DDDS 100 or related entities and a user and/or management system (user/management system) 114, e.g., a human or another entity like an application, a machine, or a device. In some embodiments, one or more communications interface(s) 110 may allow user/management system 114 to interact with computing platform(s) 101 or related entities. For example, communications interface(s) 110 may include a graphical user interface (GUI) for providing reports, notifications, and/or other information to user and/or for receiving input from the user. In another example, communications interface(s) 110 can include any suitable format, such as software applications, input/output devices, touchscreens, display monitor, tablet, mobile devices, etc.

Computing platform(s) 101 may further include a drug diversion detection module (DDDM) 104. DDDM 104 may be any suitable entity (e.g., software executing on one or more processors) for performing one or more aspects associated with drug diversion detection or related monitoring. In some embodiments, DDDM 104 may be configured for using machine learning in detecting aberrant drug dispensation events. For example, DDDM 104 may be configured for receiving, as input, an observed drug dispensation amount associated with a drug dispensation event related to a drug provider along with other drug dispensation event data, wherein the drug dispensation event data comprises drug provider information, procedure information, and patient information; generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm and is trained using one or more data sets associated with related drug dispensation events; and outputting, by the drug diversion detection algorithm, information indicating that the observed drug dispensation amount is aberrant.

In some embodiments, DDDM 104 may be configured for using machine learning in detecting that a drug dispensation pattern is consistent with drug diversion. For example, DDDM 104 may be configured for generating, using information about historical drug dispensation events associated with a drug or class of drugs and a drug provider, a drug dispensation pattern over time associated with the drug provider; detecting, using a trained drug diversion detection algorithm and the drug dispensation pattern, whether the drug dispensation pattern is consistent with drug diversion; and outputting, by the drug diversion detection algorithm, information indicating that the drug dispensation pattern is consistent with drug diversion by the drug provider.

In some embodiments, DDDM 104 may be configured for using machine learning in classifying drug dispensation patterns into different drug dispensation groups. For example, DDDM 104 may be configured for classifying, using a trained drug diversion detection algorithm, drug dispensation patterns associated with drug providers into different drug dispensation groups and notifying a user or a related system about one or more drug dispensation groups or one or more drug providers thereof if a predefined threshold value indicating drug diversion is reached or exceeded.

In some embodiments, DDDM 104 may determine and/or provide assessment or outcome information, a notification, an alert, and/or related information to one or more entities, such as a user, a system operator, a medical records system, a management system, or any combination thereof. For example, assessment or outcome information can be presented via communications interface(s) 110 to user/management system 114 via any suitable format for visualization, such as a graphical display, tables, charts, etc. In some embodiments, anomalous results can optionally be highlighted. In some embodiments, outcome data, reports, and/or other information can be computed in an on-going manner and/or provided to the user dynamically or periodically. In some embodiments, assessment or outcome information may be presented to user/management system 114 with an audible alert; a visual alert; and/or a tactile alert.

Memory 106 may be any suitable entity or entities (e.g., non-transitory computer readable media) for storing various information. Memory 106 may include an DDDM related storage 108. DDDM related storage 108 may be any suitable entity (e.g., a database embodied or stored in computer readable media) usable for storing drug dispensation event data, machine learning algorithms, drug diversion detection algorithms and/or models, expected drug amounts, clinician information, treatment recommendations, classification logic, and/or predetermined information or settings for DDDS 100 or DDDM 104. For example, DDDM related storage 108 may include or obtain at least some data from two or more separate data sources 112. In some embodiments, memory 106 may be utilized to store DDDM 104 (or software therein) and an DDDM related storage 108.

In some embodiments, DDDS 100 or DDDM 104 may include or utilize a data storage and retrieval system (e.g., a database) where information collected from various data sources is compiled. In such embodiments, the compiled data may be collected and compiled periodically or aperiodically (e.g., dynamically or continuously), and the DDDS 100 or DDDM 104 can analyze the data to detect aberrant drug dispensation events and/or drug dispensation patterns consistent with drug diversion.

In some embodiments, DDDS 100 or DDDM 104 may perform drug diversion surveillance or monitoring based on procedures for which the medications are used rather than solely on the drug provider. For example, in contrast to conventional monitoring systems that solely rely on pharmacy records related to the drug provider and do not take into account specific day-to-day patient scenarios that can cause variations in drug dispensation amounts, DDDS 100 or DDDM 104 may use a trained drug diversion detection algorithm that can use drug dispensation event data to detect aberrant drug dispensation amounts. For example, if an anesthesia provider has a week with an unusually high number of complex spinal fusion procedures, these events may appear as a spike in dispensation of opioids, which can lead to a false-positive indication of drug diversion in the previously mentioned conventional monitoring systems. However, drug dispensation event data used by DDDS 100 or DDDM 104 can include types of patients the drug provider is supporting and specific procedures that are being performed and the trained drug diversion detection algorithm can consider this information when determining whether the drug dispensation events were aberrant or whether the related drug dispensation pattern was consistent with drug diversion.

In some embodiments, drug dispensation event data may include clinical data collected from an EMR system, and drug transaction data collected from an MDS database. Example drug dispensation event data can include a variety of information, such as pharmacy-related data including a drug provider name, a medication name and quantity, and a dispensing location, a dispensation frequency, and a dispensation date and time. Patient related information can include, but is not limited to, a procedure requiring drug dispensation (e.g., a surgical procedure), a date of procedure, a procedure duration, a patient's age and weight at the time of procedure, a patient's baseline medications, a procedure location, drug providers associated with the procedure, a procedure's urgency or necessity, and/or a patient status, e.g., according to the American Society of Anesthesiologists (ASA) physical status classification system. Medication names can optionally be normalized to a standard naming convention (e.g., using RXNav). Additionally, the medications can be grouped according to abuse potential and/or a drug classification. For example, medications can be grouped into opioid, benzodiazepine, and ketamine equivalents. In some embodiments, scheduling data can optionally be used to compare expected work habits with actual instances (e.g., was a drug dispensed in the area where the drug provider was working that day?). In some embodiments, data queries and analyses can be computed in an on-going manner and may be provided periodically or aperiodically.

In some embodiments, a trained drug diversion detection algorithm for detecting aberrant drug dispensation events may utilize quantified and/or learned relationships between drug dispensation amounts and dispensation events (e.g., procedures). For example, a neural network may be trained using a data set where dispensation events (e.g., procedures) are grouped by procedural terminology codes (e.g., using a clinical classification software tool) and actual dispensation amounts are represented as or converted to relevant equivalents (e.g., opioid, benzodiazepine, and ketamine amounts). In this example, the neural network can be trained to determine the quantity of equivalents needed per procedure, thus establishing patterns of "expected" dispensation amounts for specific clinical area and/or rotation scenarios. The neural network may further determine differentiation of random and special cause variation in temporal trends. In some embodiments, expected drug dispensation amounts can be controlled for several potential confounding variables, e.g., a patient age, an ASA patient status, a patient weight, a patient discharge disposition, a procedure duration and type, a medical record or transaction number, etc., thereby creating a normalized, or baseline, amount of medication typically used for a particular procedure.

In some embodiments, DDDS 100, DDDM 104, or a related trained drug diversion detection algorithm may utilize aggregate drug dispensation equivalents and/or predetermined threshold values when comparing expected drug dispensation amounts and observed (e.g., documented) drug dispensation amounts. For example, a response variable of a trained drug diversion detection algorithm may correspond to aggregate equivalent amounts transacted for each drug dispensation event. If the expected drug dispensation amount for a drug dispensation event deviates from an observed value (or its equivalent) by a significant amount, the drug dispensation event may be flagged as aberrant.

In some embodiments, DDDS 100, DDDM 104, or a related trained drug diversion detection algorithm may track and/or correlate aberrant drug dispensation events for a drug provider. For example, DDDS 100 or DDDM 104 make maintain a running tally of the total number of aberrant drug dispensation events for each drug provider or group of drug providers recorded as responsible for the drug dispensation. In this example, DDDS 100 or DDDM 104 may track individual or group patterns of drug dispensation and highlight or flag those that deviate from expected or usual practice given the clinical context. It will be understood to a person of skill in the art that the deviation threshold for flagging can be set according to the use context. For example, in some instances, a deviation can be considered significant if the drug dispensation amount is one standard deviation away from the expected drug dispensation amount. In other instances, the deviation can be flagged at two or three standard deviations away from the expected or average drug dispensation amount.

In some embodiments, DDDS 100, DDDM 104, or a related trained drug diversion detection algorithm may tract, detect, and/or flag unusual or aberrant drug dispensation patterns over time. For example, DDDS 100 or DDDM 104 may use clustering algorithm (e.g., based on a hidden Markov model, Gaussian mixture model, or another suitable clustering or mixture model) to analyze drug dispensation patterns of multiple drug providers. In this example, the clustering algorithm may indicate that a drug diverter's dispensation amounts cluster differently than their peers. In some instances, the drug diverter's aberrant usage may increase over time. This may be because the drug diverter's tolerance increases, for example, or because the diverter becomes emboldened due to lack of discovery. Hence, a clustering model can be created for each drug provider to expose changing drug dispensation behavior. In some embodiments, an affinity matrix can be created by calculating a log likelihood for each pair-wise provider trajectory to automatically group providers.

In some embodiments, DDDS 100 or DDDM 104 may generate a ranked list of outlier providers of interest at a specific point in time, as well as to continuously monitor for changes in a drug dispensation pattern that may reflect diversion behavior. In some embodiments, outliers can be identified in terms of magnitude of drugs issued, pattern of drug utilization, and/or incidence of errors in accounting.

In some embodiments, DDDS 100 or DDDM 104 may also identify and potentially ignore or flag non-standard or unusual behaviors that appear to be diversions but may be process workarounds (e.g., transactions made by drug providers not assigned to patients who are legitimately receiving a medication). In some embodiments, these behaviors may be reported if deemed to be of interest, e.g., to organization leadership based on user preferences.

In some embodiments, DDDM related storage 108 may be accessible by DDDM 104 and/or other modules of computing platform(s) 101 and may be located externally to or integrated with DDDM 104 and/or computing platform(s) 101. For example, DDDM related storage 108 may be stored at a server located remotely from DDDM 104 but still accessible by DDDM 104. In another example, DDDM related storage 108 may be distributed or separated across multiple nodes.

In some embodiments, DDDS 100 or DDDM 104 may be configured for generating, using the one or more data processors, one or more training data sets and/or one or more testing data sets based at least in part on a set of drug dispensation events and related dispensation data; determining, using one or more data processors, one or more initial detection models using one or more machine learning algorithms based at least in part on the one or more training data sets; applying, using one or more data processors, one or more initial detection models on the one or more training data sets to generate result data; performing, using one or more processors, an ensemble algorithm on the result data to generate ensemble data; determining, using the one or more data processors, one or more final detection models based at least on part on the ensemble data; evaluating, using one or more of the data processors, performance of the one or more of the final detection models; detecting, using the one or more data processors, aberrant drug dispensation events and/or drug dispensation patterns consistent with drug diversion; and, optionally, notifying a user or system for implementing an appropriate plan or intervention.

In some embodiments, processor-implemented methods provided herein may be hosted on one or more servers of DDDS 100 via a network, where the detection outcomes as generated by one or more methods provided herein can assist the user(s) to build and/or evaluate one or more detection models for detecting aberrant drug dispensation events and/or drug dispensation patterns consistent with drug diversion. In some embodiments, DDDS 100 is configured to combine machine learning prediction based on one or more detection models and various drug dispensation event data.

In some embodiments, DDDS 100 may train or build one or more detection models using one or more deterministic algorithms. For example, DDDS 100 can implement one or more machine learning algorithms, such as gradient tree boosting algorithm, a random forest algorithm, support vector machine algorithm, a penalized logistic regression algorithm, a C5.0 algorithm, and combinations thereof for building the one or more detection models.

In some embodiments, a training data set can be constructed with relevant input features for a particular machine learning algorithm. For example, a classifier (e.g., a decision tree, a k-nearest neighbor algorithm, a support vector machine, or a neural network) for DDDS 100 or DDDM 104 can be trained based on a set of features for defining an expected outcome. In some embodiments, any classifier may be selected based on its ease of training, implementation, and interpretability. In some embodiments, a classifier may utilize a combination of a deep convolutional neural network (CNN) with an interpretable linear classifier. In some embodiments, Any neural network may be utilized with the present disclosure. As is recognized by those skilled in the art, neural networks work best when they have many parameters, making them powerful function approximators. However, this means that they must be trained on very large data sets. Because training models from scratch can be a very computationally intensive process, it is within the scope of the present disclosure that pre-trained models may also be utilized.

In some embodiments, cross-validation techniques may be used to construct a decision tree. Although the method discusses a single classifier, alternative embodiments exist wherein a collection of classifiers (e.g., decision trees) may be utilized to provide higher accuracy than a single classifier. For example, the method may employ ensemble classifiers consisting of several neural networks.

In some embodiments, DDDS 100 may assist one or more of the users to build and/or evaluate one or more detection models through a graphical user interface. For example, user/management system 114 may provide or initiate providing inputs (e.g., drug dispensation event data) at a GUI for DDDS 100 to build or train one or more detection models.

In some embodiments, users may interact with DDDS 100 through a number of ways, such as via one or more networks. In such embodiments, one or more servers accessible through the network(s) can host DDDS 100. The one or more servers can also contain or have access to the one or more data stores for storing data for DDDS 100, or receive input data (e.g., drug dispensation event data) from external sources. It should be appreciated that in some embodiments DDDS 100 or a related server may be self-contained and not connected to external networks due to security or other concerns.

It will be appreciated that the above described modules in FIG. 1 are for illustrative purposes and that features or portions of features described herein may be performed by different and/or additional modules, components, or nodes. For example, aspects of drug diversion detection and/or related monitoring herein may be performed by DDDM 104, computing platform(s) 101, and/or other modules or nodes. Further, it will be understood that while various machine learning algorithms are discussed above, other known machine learning algorithms may also be used in detecting drug diversion.

Figure 2:
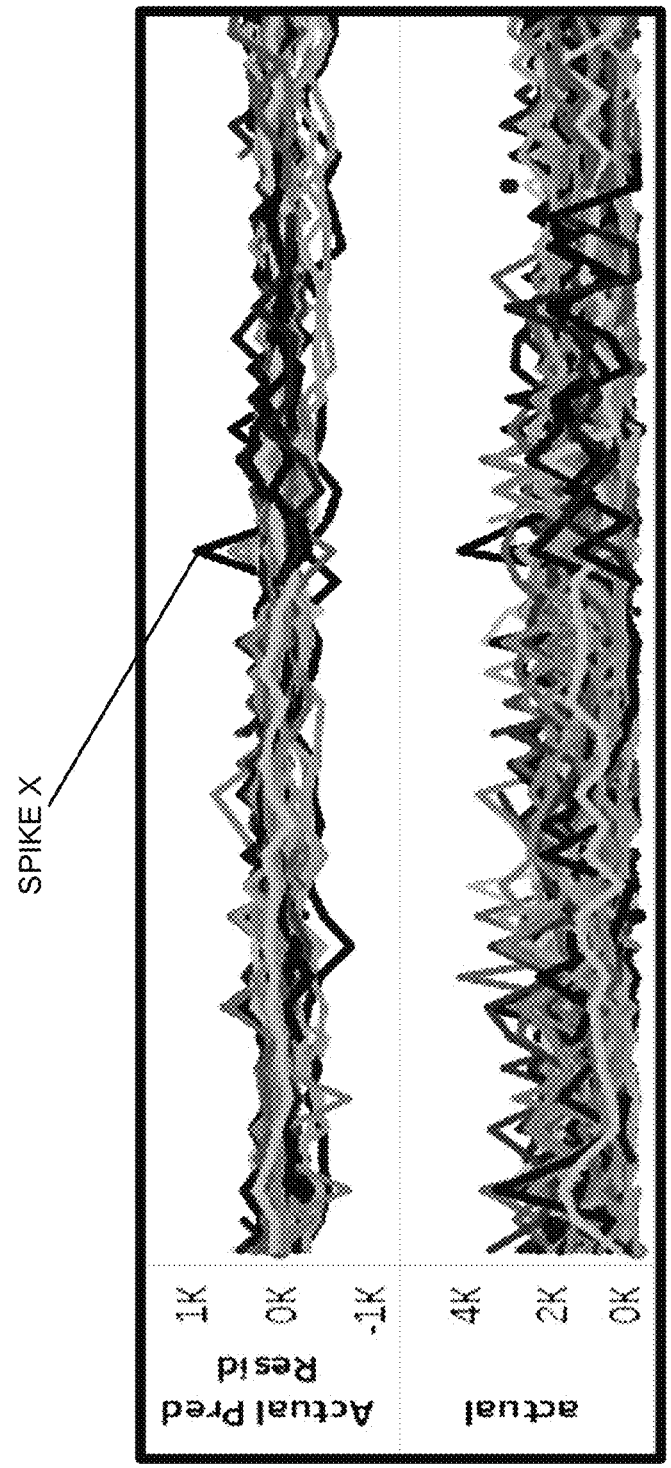
FIG. 2 depicts information associated with example residual drug dispensation amounts.

FIG. 2 depicts information associated with example residual drug dispensation amounts. In some embodiments, DDDS 100 or DDDM 104 may generate graphs for showing drug dispensation information and trends. For example, when showing drug dispensation amounts, DDDS 100 or DDDM 104 may normalize or otherwise adjust drug dispensation amounts by calculating residual drug dispensation amounts and/or related drug equivalency values, e.g., converting ketamine amounts into an equivalent morphine or opioid amount. In some embodiments, a residual drug dispensation amount may be calculated by subtracting an expected drug dispensation amount for a drug dispensation event from an observed drug dispensation amount for a drug dispensation event.

Referring to FIG. 2, a diagram 200 shows a top line graph indicating residual drug dispensation amounts for a number of drug dispensation events (e.g., surgical procedures), where each line represents the responsible drug provider and a bottom line graph indicating observed drug dispensation amounts for the same drug dispensation events (e.g., surgical procedures), where each line represents the responsible drug provider. As shown, a particular spike 'x' in diagram 200? represents a set of seven drug dispensation events in one week that involved unexpectedly high drug dispensation amounts, e.g., four of the events occurring with five days resulted in a total of 425 milligrams (mg) of morphine equivalents greater than the expected drug dispensation amounts.

It will be appreciated that FIG. 2 is for illustrative purposes and that different and/or additional information than that described above or depicted in FIG. 2 can be displayed.

Figure 3:
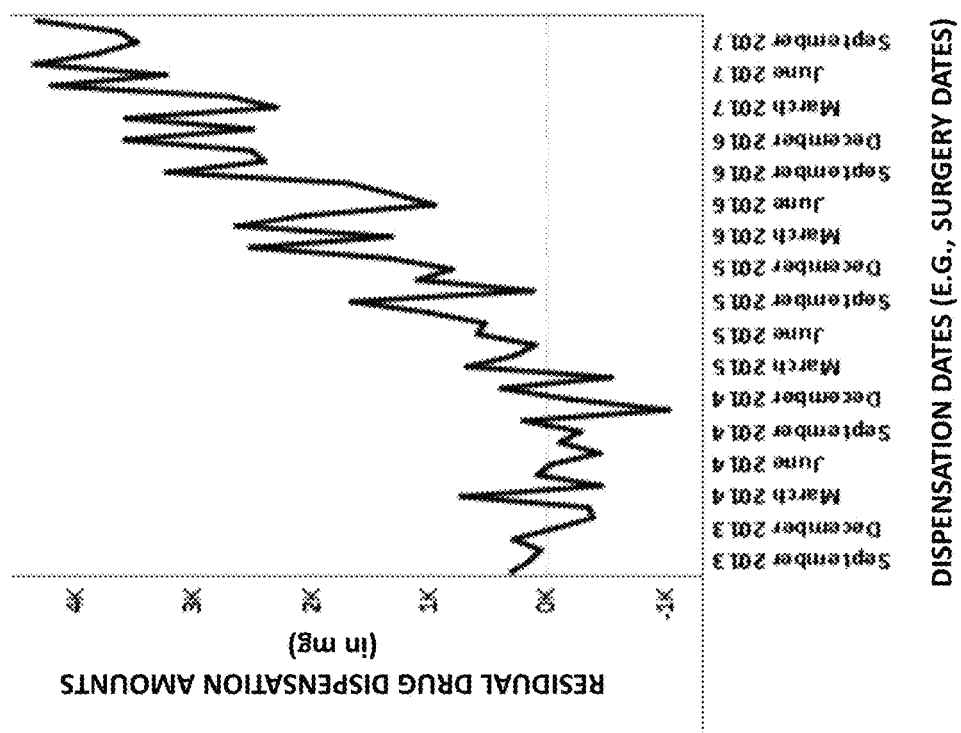
FIG. 3 depicts information associated with an example drug dispensation pattern.

FIG. 3 depicts information associated with an example drug dispensation pattern. In some embodiments, DDDS 100 or DDDM 104 may generate graphs for showing drug dispensation patterns (e.g., behavior trends) of one or more drug providers. For example, when showing a drug dispensation pattern, DDDS 100 or DDDM 104 may normalize or otherwise adjust drug dispensation amounts by calculating residual drug dispensation amounts and/or related drug equivalency values, e.g., converting ketamine amounts into an equivalent morphine or opioid amount. In some embodiments, a residual drug dispensation amount may be calculated by subtracting an expected drug dispensation amount for a drug dispensation event from an observed drug dispensation amount for a drug dispensation event.

Referring to FIG. 3, a diagram 300 shows a line graph indicating residual drug dispensation amounts for a number of drug dispensation events (e.g., surgical procedures). As shown, the line graph shows a pattern of drug dispensation events with substantially increasing residual drug dispensation amounts. While such a pattern may be consistent with drug diversion, DDDS 100 or DDDM 104 may also analyze and/or provide to user/management system 114 additional information indicating that this pattern could be caused by other factors, e.g., a graph or data indicating that for a majority of these events a different person was responsible for procuring the drugs, e.g., from a drug dispensing system.

It will be appreciated that FIG. 3 is for illustrative purposes and that different and/or additional information than that described above or depicted in FIG. 3 can be displayed.

FIGS. 4A-4D depict graphs representing example drug dispensation event data. In some embodiments, DDDS 100 or DDDM 104 may generate graphs for showing drug dispensation patterns (e.g., behavior trends) of one or more drug providers. For example, when showing a drug dispensation pattern, DDDS 100 or DDDM 104 may normalize or otherwise adjust drug dispensation amounts by calculating residual drug dispensation amounts and/or related drug equivalency values, e.g., ketamine amounts may be converted into an equivalent morphine or opioid amount. In some embodiments, a residual drug dispensation amount may be calculated by subtracting an expected drug dispensation amount for a drug dispensation event from an observed drug dispensation amount for a drug dispensation event.

In some embodiments, DDDS 100 or DDDM 104 may bring a user's attention, via a GUI, to a potential drug diverter by providing a series of graphs 400-406 where differences between a potential drug diverter's drug dispensation behavior and other drug providers' drug dispensation behaviors become more discernible to the user, user/management system 114.

Figure 4A:
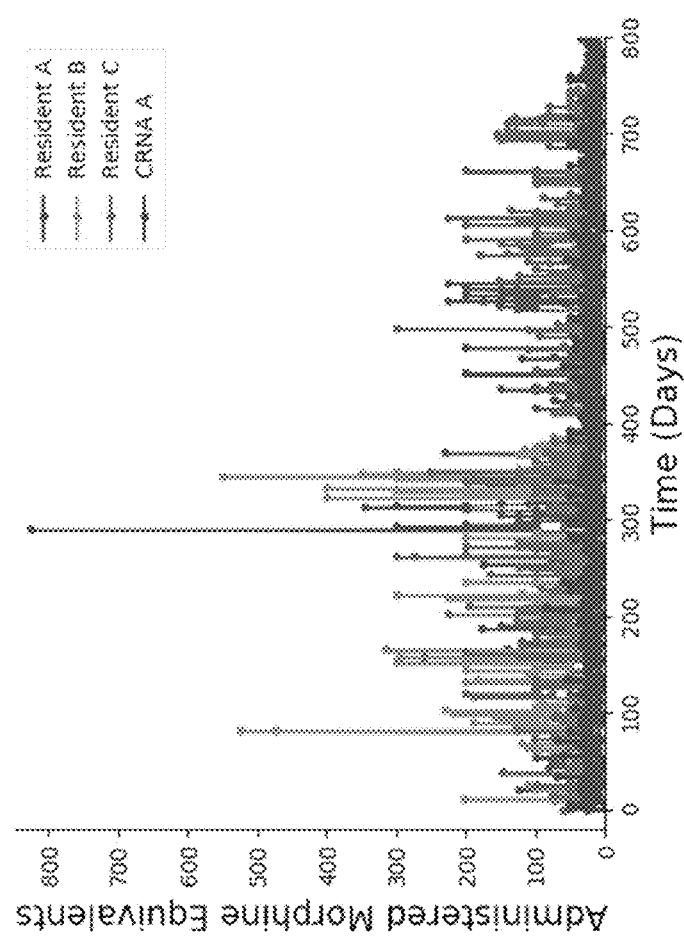
FIGS. 4A-4D depict graphs representing example drug dispensation event data.

Referring to FIG. 4A, a line graph 400 indicates administered (e.g., observed) drug dispensation amounts as morphine equivalents for a number of drug providers over a time period of 800 days.

Figure 4B:
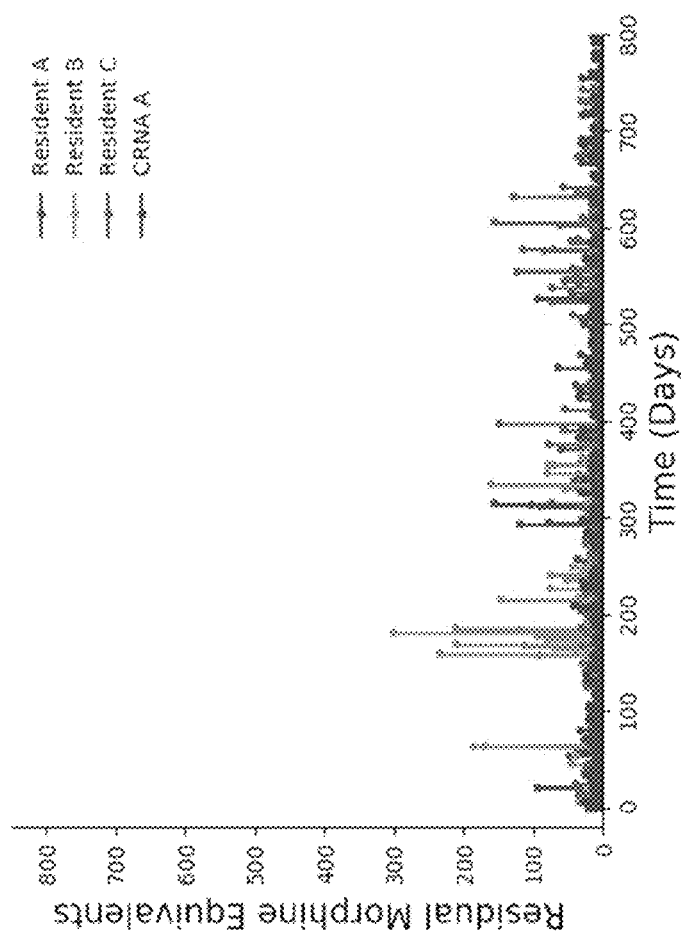

Referring to FIG. 4B, a line graph 402 indicates residual (e.g., observed—expected) drug dispensation amounts as morphine equivalents for the same drug providers over the same time period.

Figure 4C:
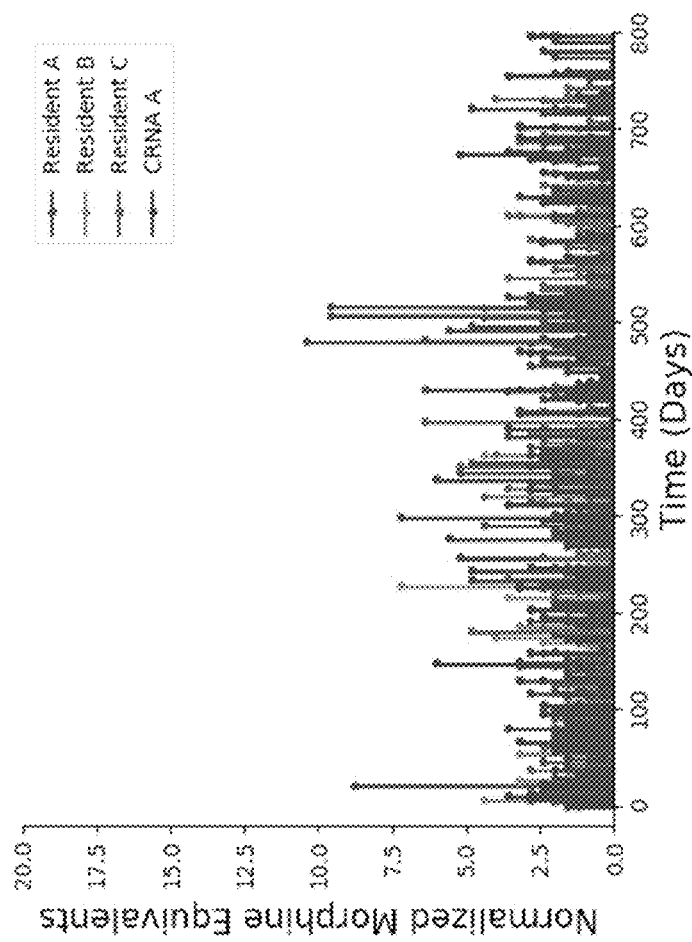

Referring to FIG. 4C, a line graph 404 indicates drug dispensation amounts as normalized morphine equivalents for the same drug providers over the same time period. For example, by normalizing, a different scale is used so that differences in drug dispensation amounts are more distinct.

Figure 4D:
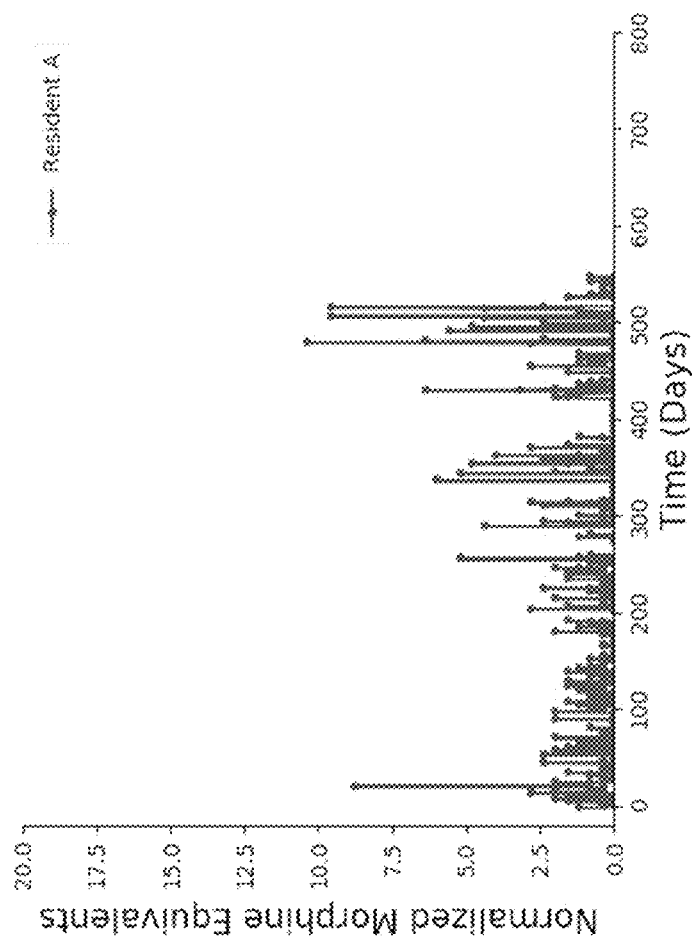
Figure 5A:
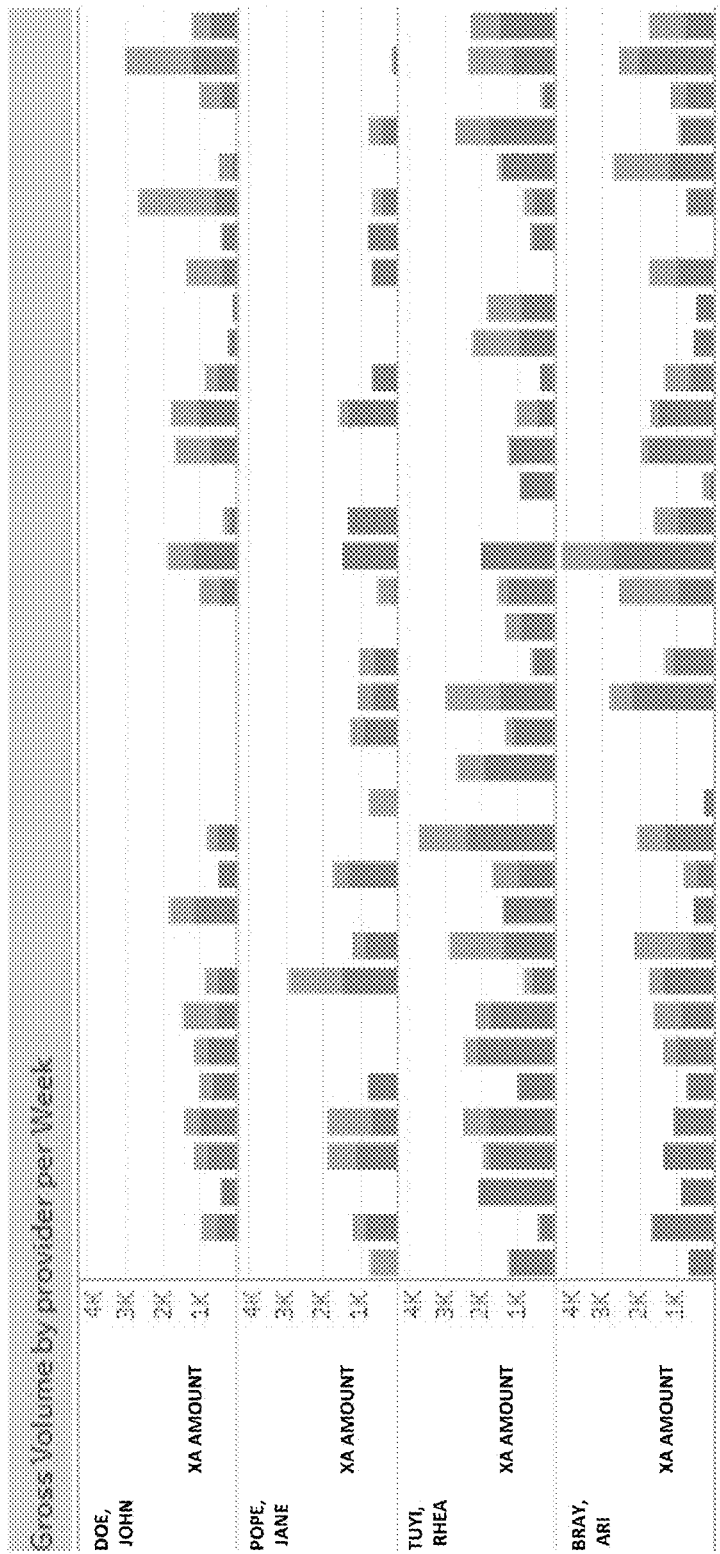
Figure 5C:
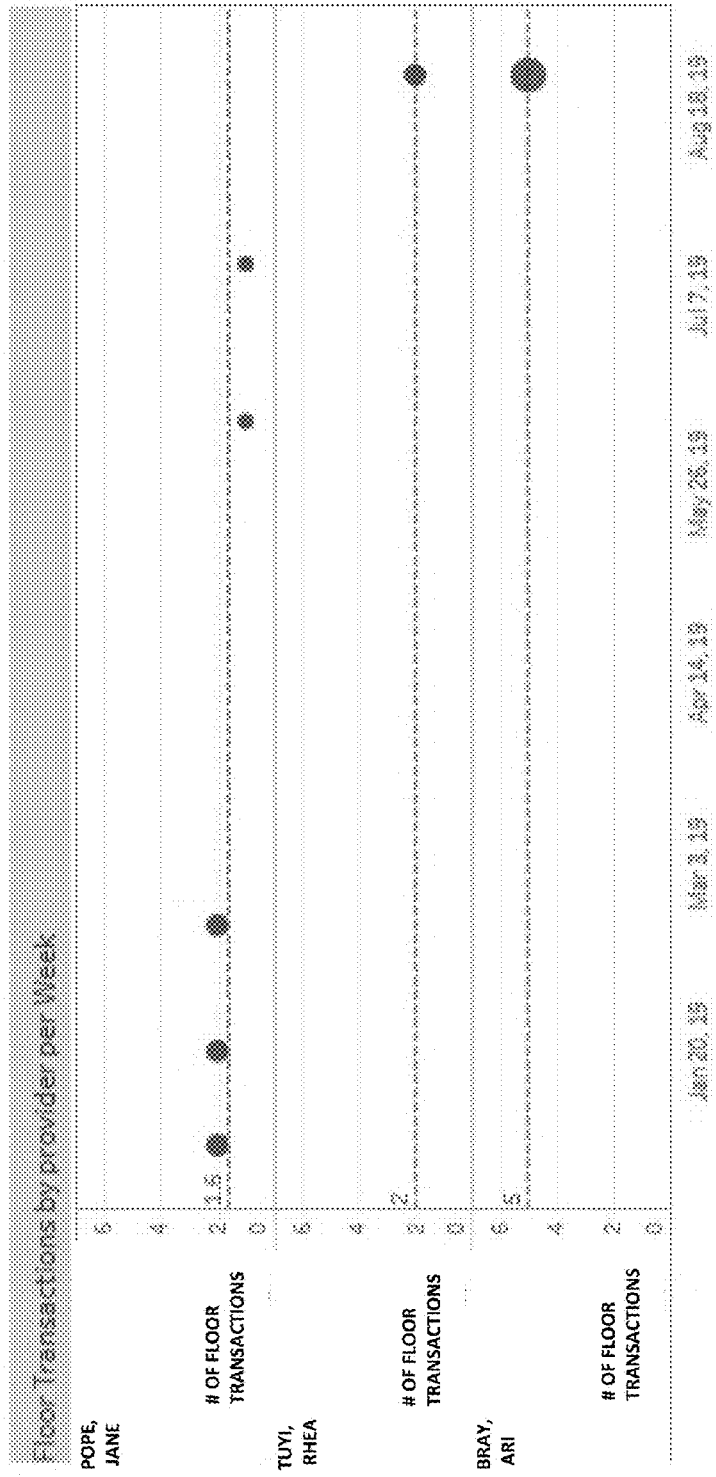
Figure 5D:

Referring to FIG. 4D, a line graph 406 indicates drug dispensation amounts as normalized morphine equivalents for a single drug provider over the same time period. For example, diagram 406 may be useful to highlight a potential drug diverter's pattern for further review by user/management system It will be appreciated that FIGS. 4A-4D are for illustrative purposes and that different and/or additional information than that described above or depicted in FIG. 4 can be displayed.

FIGS. 5A-5D depict charts 500-506, respectively, from a screenshot of an example drug diversion dashboard. In some embodiments, DDDS 100, DDDM 104, or a related trained drug diversion detection algorithm may generate outcome information and/or other data related to analysis of drug dispensation event data. In some embodiments, outcome information and/or other data may be provided via communications interface(s) 110 via one or more visualization techniques, e.g., a drug diversion dashboard may display relevant drug diversion reports or related monitoring information to user/management 114.

Referring to FIGS. 5A-5D, a drug diversion dashboard may represent a GUI for displaying various information (e.g., derived dispensation metrics and/or analytics) based on drug dispensation event data and/or one or more machine learning based algorithms. For example, a drug diversion dashboard may represent outcome data and/or other information based on electronically captured drug dispensation event data from relevant sources 112 including but not limited to electronic health records and pharmacy transactions. In some embodiments, a drug diversion dashboard may display visual analytics for identifying potential instances or patterns of drug diversion by drug providers. In some embodiments, a drug diversion dashboard may represent a dynamic, visual dashboard displaying individual and/or group patterns of drug dispensation and highlighting those patterns or providers that deviate from expected or usual drug dispensation behavior given the clinical context. In some embodiments, a drug diversion dashboard may also indicate unusual patterns based on expected behavior for each clinical area/rotation and/or indicate when random and special cause variation in temporal trends.

It will be appreciated that is FIGS. 5A-5D are for illustrative purposes and that different and/or additional information than that described above or depicted in FIGS. 5A-5D can be displayed.

Figure 6:
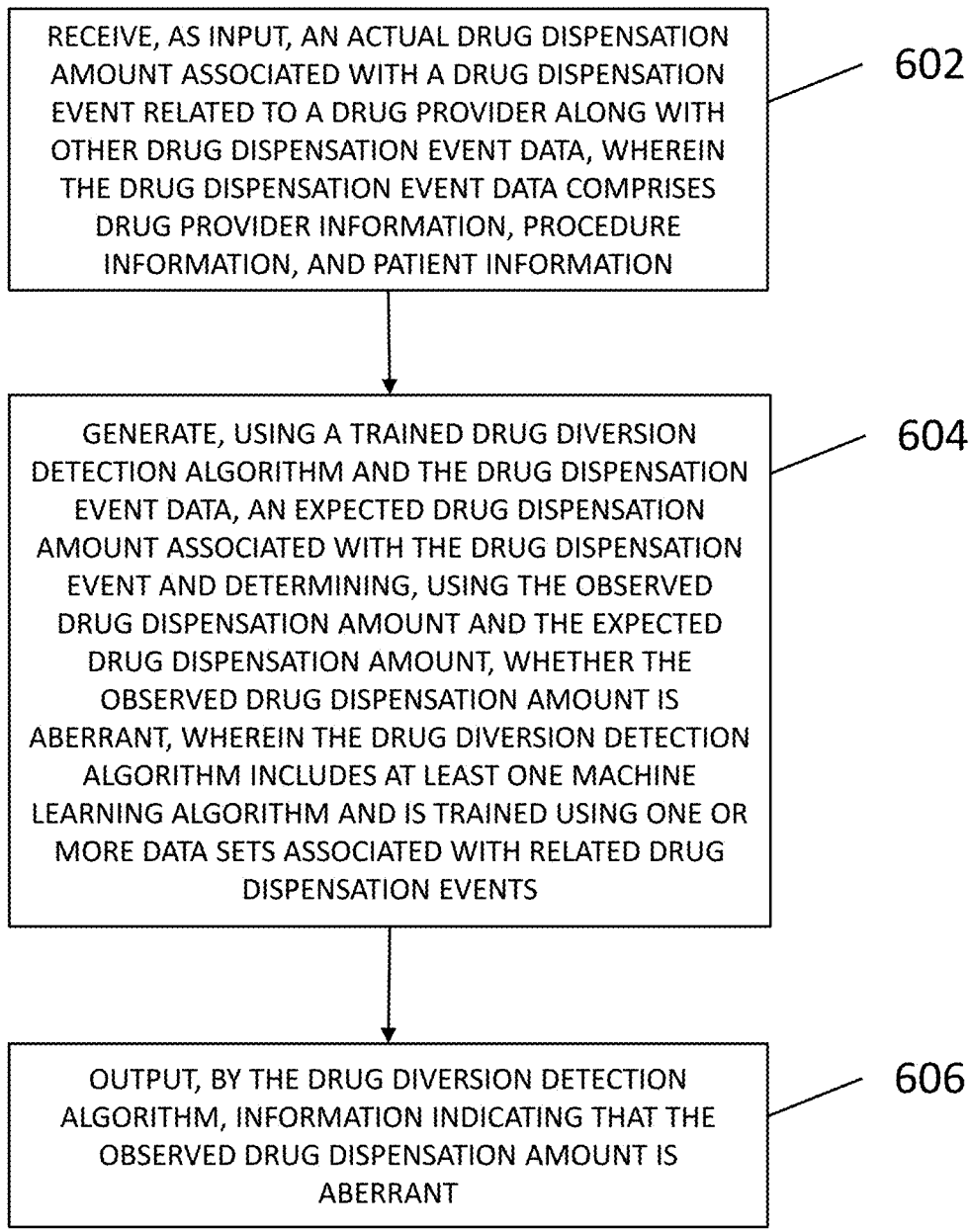
FIG. 6 is a diagram illustrating an example process for using machine learning in detecting an aberrant drug dispensation event.

FIG. 6 is a diagram illustrating an example process 600 for using machine learning in detecting an aberrant drug dispensation event. In some embodiments, process 600 described herein, or portions thereof, may be performed at or by DDDS 100, computing platform(s) 101, DDDM 104, and/or another module or node. For example, DDDS 100 or computing platform(s) 101 may be a mobile device, a computer, or other equipment (e.g., a drug surveillance or management system) and DDDM 104 may include or provide an application running or executing on computing platform(s) 101. In some embodiments, process 600 may include steps 602, 604, and 606.

In step 602, an observed drug dispensation amount associated with a drug dispensation event related to a drug provider along with other drug dispensation event data may be received as input, wherein the drug dispensation event data comprises drug provider information, procedure information, and patient information.

In some embodiments, at least some drug dispensation event data may be obtained from a drug dispensing database, an electronic health record medical database, or a database containing information obtained from multiple disparate data management systems. In some embodiments, drug provider information may include a drug provider identifier, a drug provider job role, and/or a drug provider employment status. In some embodiments, procedure information may include a medical record number, a procedure type, a drug type or class, a drug name, drug equivalency information, mitigating effects information (e.g., known tolerance to drugs used, amount of beta-blockers dispensed along with anesthesia, etc.), a drug dosage, and/or a procedure duration. In some embodiments, patient information may include a patient age (e.g., at the time of a procedure), a body weight (e.g., at the time of a procedure), a patient discharge disposition, a pain score for the patient (e.g., before, during, and/or after a procedure), patient medications (e.g., baseline or known other prescriptions), and/or a patient physical status (e.g., an ASA physical status classification).

In step 604, a drug diversion detection algorithm may be used for generating an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm and is trained using one or more data sets associated with related drug dispensation events.

In some embodiments, training a drug diversion detection algorithm for detecting an aberrant drug dispensation event may include generating, using the one or more data sets, output data from two or more machine learning algorithms; generating, using an ensemble algorithm, ensemble data based on the output data; and configuring the drug diversion detection algorithm based on the ensemble data.

In some embodiments, an ensemble algorithm used in training a drug diversion detection algorithm for detecting an aberrant drug dispensation event may include a Bayes optimal classifier, a bootstrap aggregation algorithm, a boosting algorithm, a Bayesian model combination algorithm, a Bayesian model averaging algorithm, a weighting algorithm, or a stacking algorithm.

In some embodiments, at least one machine learning algorithm usable in detecting an aberrant drug dispensation event may include a gradient tree boosting algorithm, a random forest algorithm, a support vector machine algorithm, a penalized logistic regression algorithm, a C5.0 algorithm, or a combination thereof.

In step 606, information indicating that the observed drug dispensation amount is aberrant may be outputted by the drug diversion detection algorithm.

In some embodiments, e.g., if an aberrant drug dispensation event is detected, process 600 may include notifying a user or a related system (e.g., user/management system 114) for administering to a drug provider an effective therapy or intervention or notifying a user or a related system so that an aberrant drug dispensation event or a related drug provider can be flagged for further review and/or analysis.

In some embodiments, a drug provider may include a doctor, a nurse, a medical provider, a caregiver, an anesthesia provider (e.g., a certified registered nurse anesthetist, an anesthesiologist, an anesthesia trainee, etc.), a medical specialist, a medical trainee, a patient, a veterinarian, a veterinary technician, or a medical device In some embodiments, DDDS 100 and/or computing platform(s) 101 for implementing process 600 may include a mobile device, a smartphone, a tablet computer, a laptop computer, a computer, a server, or a medical device.

It will be appreciated that process 600 is for illustrative purposes and that different and/or additional actions may be used. It will also be appreciated that various actions described herein may occur in a different order or sequence.

Figure 7:
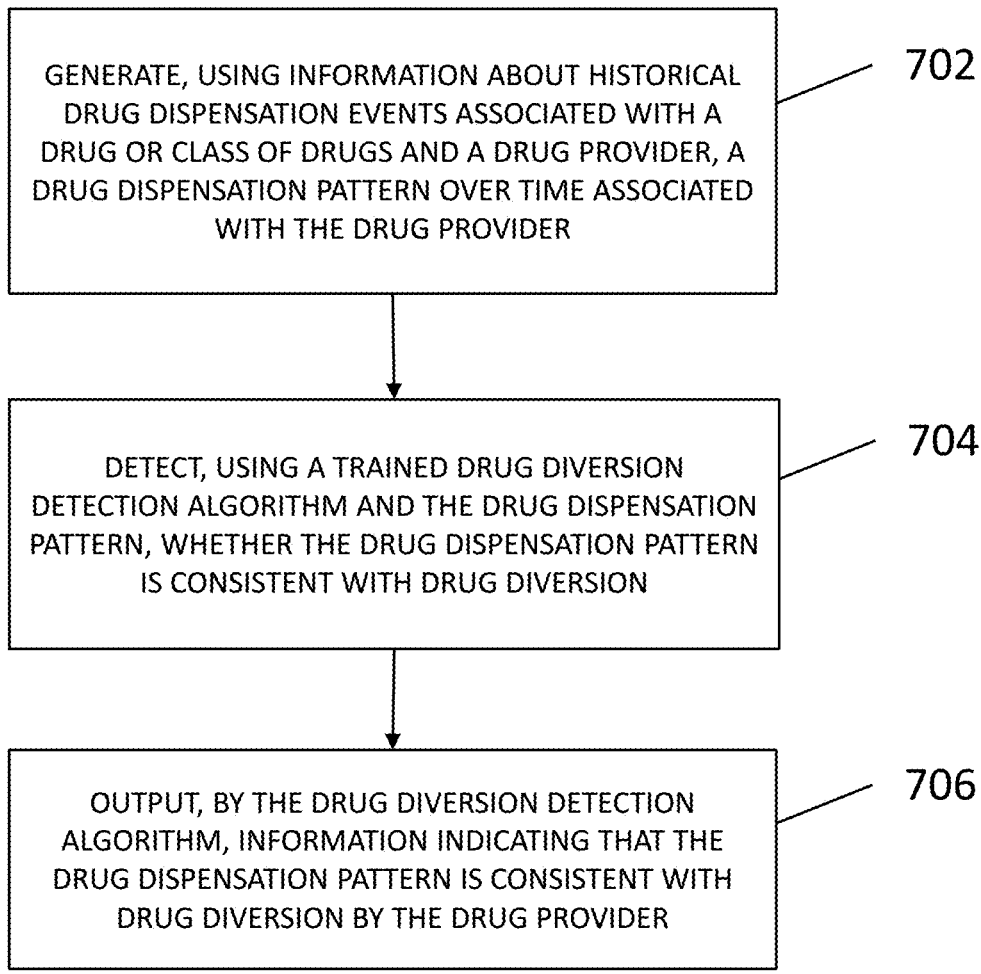
FIG. 7 is a diagram illustrating an example process for using machine learning in detecting that a drug dispensation pattern is consistent with drug diversion.

FIG. 7 is a diagram illustrating an example process 700 for using machine learning in detecting that a drug dispensation pattern is consistent with drug diversion. In some embodiments, process 700 described herein, or portions thereof, may be performed at or by DDDS 100, computing platform(s) 101, DDDM 104, and/or another module or node. For example, DDDS 100 or computing platform(s) 101 may be a mobile device, a computer, or other equipment (e.g., a drug surveillance or management system) and DDDM 104 may include or provide an application running or executing on computing platform(s) 101. In some embodiments, process 700 may include steps 702, 704, and 706.

In step 702, a drug dispensation pattern over time associated with a drug provider may be generated using information about historical drug dispensation events associated with the drug provider and a drug (e.g., morphine) or a class of drugs (e.g., opioids).

In some embodiments, information about historical drug dispensation events may include drug dispensation event data for multiple historical drug dispensation events. For example, for each historical drug dispensation event (e.g., a surgical procedure requiring anesthesia), drug dispensation event data may comprises drug provider information (e.g., a drug provider identifier, a drug provider job role, and/or a drug provider employment status), procedure information (e.g., a procedure type, a drug type or class, a drug name, drug equivalency information, a drug dosage, and/or a procedure duration), and patient information (e.g., a patient age, a body weight, a patient discharge disposition, a pain score for the patient, patient medications and/or a patient physical status).

In some embodiments, at least some historical drug dispensation event data may be obtained from a drug dispensing database, an electronic health record medical database, or a database containing information obtained from multiple disparate data management systems.

In step 704, a trained drug diversion detection algorithm may be used for detecting whether the drug dispensation pattern is consistent with (e.g., indicates or appears to indicate) drug diversion. For example, a drug diversion detection algorithm includes at least one machine learning algorithm and is trained using one or more data sets associated with related drug dispensation events.

In some embodiments, training a drug diversion detection algorithm for detecting whether a drug dispensation pattern is consistent with drug diversion may include generating, using the one or more data sets, output data from two or more machine learning algorithms; generating, using an ensemble algorithm, ensemble data based on the output data; and configuring the drug diversion detection algorithm based on the ensemble data.

In some embodiments, an ensemble algorithm used in training a drug diversion detection algorithm for detecting whether the drug dispensation pattern is consistent with drug diversion may include a Bayes optimal classifier, a bootstrap aggregation algorithm, a boosting algorithm, a Bayesian model combination algorithm, a Bayesian model averaging algorithm, a weighting algorithm, or a stacking algorithm.

In some embodiments, at least one machine learning algorithm usable in detecting an aberrant drug dispensation event may include a gradient tree boosting algorithm, a random forest algorithm, a support vector machine algorithm, a penalized logistic regression algorithm, a C5.0 algorithm, or a combination thereof.

In step 706, information indicating that the drug dispensation pattern is consistent with drug diversion by the drug provider may be outputted by the drug diversion detection algorithm.

In some embodiments, e.g., if it is detected that a drug dispensation pattern is consistent with drug diversion by a drug provider, process 700 may include notifying a user or a related system (e.g., user/management system 114) for administering to a drug provider an effective therapy or intervention or notifying a user or a related system so that future drug dispensation events or a related drug provider can be flagged for review and/or analysis.

In some embodiments, a drug provider may include a doctor, a nurse, a medical provider, a caregiver, an anesthesia provider (e.g., a certified registered nurse anesthetist, an anesthesiologist, an anesthesia trainee, etc.), a medical specialist, a medical trainee, a patient, a veterinarian, a veterinary technician, or a medical device In some embodiments, DDDS 100 and/or computing platform(s) 101 for implementing process 700 may include a mobile device, a smartphone, a tablet computer, a laptop computer, a computer, a server, or a medical device.

It will be appreciated that process 700 is for illustrative purposes and that different and/or additional actions may be used. It will also be appreciated that various actions described herein may occur in a different order or sequence.

Figure 8:
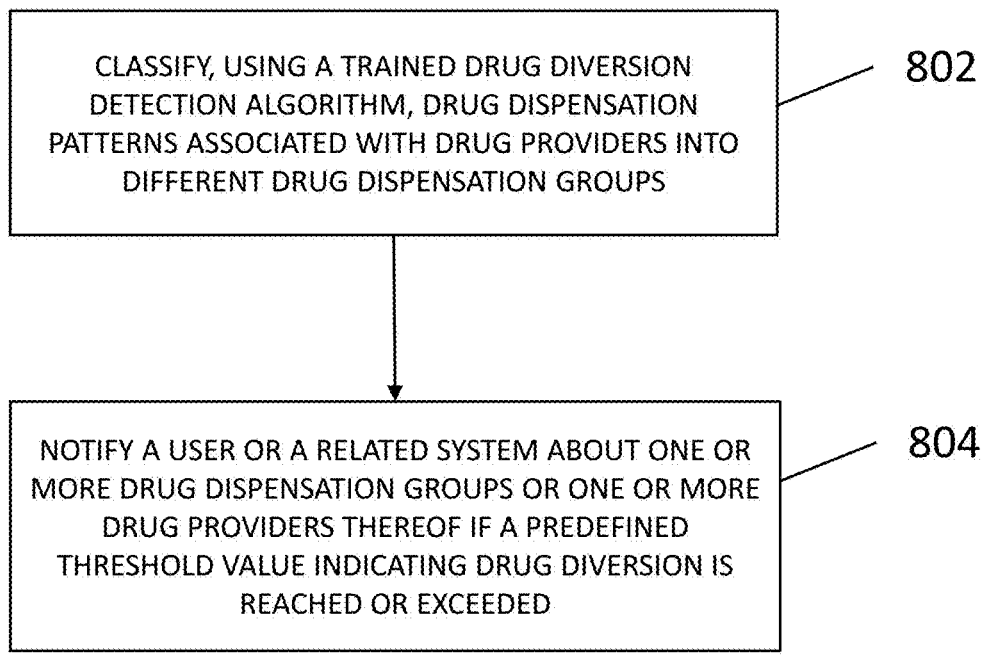
FIG. 8 is a diagram illustrating an example process for using machine learning in detecting drug diversion using classification.

FIG. 8 is a diagram illustrating an example process 800 for using machine learning in detecting drug diversion using classification. In some embodiments, process 800 described herein, or portions thereof, may be performed at or by DDDS 100, computing platform(s) 101, DDDM 104, and/or another module or node. For example, DDDS 100 or computing platform(s) 101 may be a mobile device, a computer, or other equipment and DDDM 104 may include or provide an application running or executing on computing platform(s) 101. In some embodiments, process 800 may include steps 802 and 804.

In some embodiments, drug dispensation patterns associated with drug providers may be generated by DDDS 100 or a related entity using information about historical drug dispensation events. For example, for each historical drug dispensation event (e.g., a surgical procedure requiring anesthesia), drug dispensation event data may comprises drug provider information (e.g., a drug provider identifier, a drug provider job role, and/or a drug provider employment status), procedure information (e.g., a medical record number, a procedure type, a drug type or class, a drug name, drug equivalency information, a drug dosage, and/or a procedure duration), and patient information (e.g., a patient age, a body weight, a patient discharge disposition, a pain score for the patient, patient medications and/or a patient physical status).

In step 802, a trained drug diversion detection algorithm may be used for classifying drug dispensation patterns associated with drug providers into different drug dispensation groups. For example, a drug diversion detection algorithm includes at least one machine learning algorithm and is trained using one or more data sets associated with related drug dispensation events.

In some embodiments, training a drug diversion detection algorithm for classifying drug dispensation patterns associated with drug providers may utilize a clustering or mixture model and/or to identify changing behavior of a drug provider. For example, a clustering model may be a Hidden Markov Model, a Gaussian Mixture Model, a custom-developed model, or another model. In another example, an affinity matrix may be used to automatically group drug providers, where the affinity matrix is created by calculating a log likelihood for each pair-wise provider trajectory.

In some embodiments, training a drug diversion detection algorithm for classifying drug dispensation patterns associated with drug providers may include generating, using the one or more data sets, output data from two or more machine learning algorithms; generating, using an ensemble algorithm, ensemble data based on the output data; and configuring the drug diversion detection algorithm based on the ensemble data.

In some embodiments, an ensemble algorithm used in training a drug diversion detection algorithm for classifying drug dispensation patterns associated with drug providers may include a Bayes optimal classifier, a bootstrap aggregation algorithm, a boosting algorithm, a Bayesian model combination algorithm, a Bayesian model averaging algorithm, a weighting algorithm, or a stacking algorithm.

In some embodiments, at least one machine learning algorithm usable in classifying drug dispensation patterns associated with drug providers may include a gradient tree boosting algorithm, a random forest algorithm, a support vector machine algorithm, a penalized logistic regression algorithm, a C5.0 algorithm, or a combination thereof.

In step 804, a user or a related system may be notified about one or more drug dispensation groups or one or more drug providers thereof if a predefined threshold value indicating drug diversion is reached or exceeded. For example, if a classification group is consistent with (e.g., indicates or appears to indicate) drug diversion, a user or a related system (e.g., user/management system 114) may be notified for administering to one or more drug providers of the classification group an effective therapy or intervention. In another example, a classification group is consistent with drug diversion, a user or a related system (e.g., user/management system 114) may be notified so that one or more drug providers of the classification group can be flagged for intervention, review, and/or further analysis.

In some embodiments, a drug provider may include a doctor, a nurse, a medical provider, a caregiver, an anesthesia provider (e.g., a certified registered nurse anesthetist, an anesthesiologist, an anesthesia trainee, etc.), a medical specialist, a medical trainee, a patient, a veterinarian, a veterinary technician, or a medical device.

In some embodiments, DDDS 100 and/or computing platform(s) 101 for implementing process 800 may include a mobile device, a smartphone, a tablet computer, a laptop computer, a computer, a server, or a medical device.

It will be appreciated that process 800 is for illustrative purposes and that different and/or additional actions may be used. It will also be appreciated that various actions described herein may occur in a different order or sequence.

It should be noted that DDDS 100, computing platform(s) 101, DDDM 104, and/or functionality described herein may constitute a special purpose computing device. Further, DDDS 100, computing platform(s) 101, DDDM 104, and/or functionality described herein can improve the technological field of detecting or identifying drug diversion by a drug provider using machine learning. For example, a device implementing a machine learning based drug diversion detection model (e.g., algorithm) can analyze drug dispensation event data to identify or detect anomalous or aberrant behavior consistent with drug diversion by a drug provider.

The disclosure of each of the following references is incorporated herein by reference in its entirety to the extent not inconsistent herewith and to the extent that it supplements, explains, provides a background for, or teaches methods, techniques, and/or systems employed herein.

REFERENCES

[1] Warner DO, Berge K, Sun H, et al. Substance use disorder among anesthesiology residents, 1975-2009. JAMA 2013:310;2289-96.

[2] Booth JV, Grossman D, Moore J, et al. Substance abuse among physicians: a survey of academic anesthesiology programs. Anesth Analg. 2002;95:1024-30.

[3] Bryson EO, Silverstein JH. Addiction and substance abuse in anesthesiology. Anesthesiology. 2008;109:905-17.

[4] Silverstein JH, Silva DA, Iberti TJ. Opioid addiction in anesthesiology. 1993;79:354-75.

[5] Brenn BR, Kim MA, Hilmas E. Development of a computerized monitoring program to identify narcotic diversion in a pediatric anesthesia practice. Am J Health-Syst Pharm 2015;72:1365-72.

[6] Anesthesia Patient Safety Foundation (2017, Sep. 7). Drug Diversion in the anesthesia profession: how can APSF help everyone be safe? Supplemental Digital Content, http://links/Iww.com/AA/C616

[7] Epstein RH, Gratch DM, Grunwald Z. Development of a scheduled drug diversion surveillance system based on an analysis of atypical drug transactions, Anesth Analg 2007;105:1053-1060

[8] Dexter F. Detecting diversion of anesthetic drugs by providers. Anesth Analg 2007;105:897-898

[9] Smyth, P. (1997). Clustering sequences with hidden Markov models, Advances in Neural Information Processing System, Denver, 1997. Cambridge, Mass.: MIT Press.

[10] Wood, D. Drug diversion. Aust Prescr. 2015;38(5): 164-166.

[11] Becker, W.C., Starrels, J.L. Prescription drug misuse: Epidemiology, prevention, identification, and management. UpToDate article. Accessed from: https://www.uptodate.com/contents/prescription-drug-misuse-epidemiology-prevention-identification-and-management?search=drug%20diversion&source=search_result&selecte dTitle=1~150&usage_type=default&display_rank=1#H29429846.

[12] Fan, M., Tscheng, D., Hamilton, M., et al. Diversion of Controlled Drugs in Hospitals: A Scoping Review of Contributors and Safeguards. J. Hosp. Med. 2019;14(7): 419-428.

[13] Centers for Disease Control and Prevention. Drug Diversion. Page last reviewed: Nov 26, 2019. Accessed from: https://www.cdc.gov/injectionsafety/drugdiversion/index.html

[14] Kristof, T. Methods, Trends and Solutions for Drug Diversion. International Association for Healthcare Security and Safety Foundation. IAHSS-F RS-18-01. February 2018. Accessed from: https://iahssf.org/research/methods-trends-and-solutions-for-drug-diversion/2/

[15] BCC Research. Pharmacy Automation: Technologies and Global Markets. Published in September 2019. Accessed from: https://www-bccresearch-com. proxy.lib.duke.edu/market-research/instrumentation-and-sensors/ pharmacy-automation-tech-markets-report.html

[16] Tate, J., Warburton, P. Drug Diversion Monitoring 2019: An Early Look at Emerging vs. Established Technology. KLAS report. August 2019. Accessed from: https://klasresearch.com/report/drug-diversion-monitoring-2019/1570

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

One skilled in the art will readily appreciate that the present disclosure is well adapted to carry out various aspects and advantages mentioned, as well as those inherent therein. The present disclosure described herein are presently representative of various embodiments, are examples, and are not intended as limitations on the scope of the present disclosure. Changes therein and other uses will occur to those skilled in the art which are encompassed within the spirit of the present disclosure as defined by the scope of the claims.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for using machine learning in detecting drug diversion, the method comprising:
   at a computing platform:
      receiving, as input, an observed drug dispensation amount associated with a drug dispensation event related to a drug provider along with other drug dispensation event data, wherein the drug dispensation event data comprises drug provider information, procedure information, and patient information;
      generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm including a neural network trained using one or more data sets associated with historical drug dispensation events including a data set indicating dispensation events and corresponding drug dispensation amounts for the dispensation events; and
      outputting, by the drug diversion detection algorithm, information indicating that the observed drug dispensation amount is aberrant.

2. The method of claim 1 comprising:
   generating, using information about historical drug dispensation events associated with the drug provider and a drug or class of drugs, a drug dispensation pattern over time associated with the drug provider;
   detecting, using the drug diversion detection algorithm and the drug dispensation pattern, whether the drug dispensation pattern is consistent with drug diversion; and
   outputting, by the drug diversion detection algorithm, information indicating that the drug dispensation pattern is consistent with drug diversion by the drug provider.

3. The method of claim 2 comprising:
   notifying a user or a related system for administering to the drug provider an intervention.

4. The method of claim 2 wherein detecting that the drug dispensation pattern is consistent with drug diversion includes determining that a frequency of aberrant events is increasing and/or determining that magnitudes of detected aberrancy are increasing over a period of time.

5. The method of claim 2 comprising:
   classifying, using the drug diversion detection algorithm, the drug dispensation pattern over time associated with the drug provider and drug dispensation patterns associated with other drug providers into different drug dispensation groups; and
   notifying a user or a related system about one or more drug dispensation groups or one or more drug providers thereof if a predefined threshold value indicating drug diversion is reached or exceeded.

6. The method of claim 1 wherein training the drug diversion detection algorithm includes:
   generating, using the one or more data sets, output data from two or more machine learning algorithms;
   generating, using an ensemble algorithm, ensemble data based on the output data; and
   configuring the drug diversion detection algorithm based on the ensemble data.

7. The method of claim 1 wherein the at least one machine learning algorithm includes a convolutional neural network (CNN), a gradient tree boosting algorithm, a random forest algorithm, a support vector machine algorithm, a penalized logistic regression algorithm, a C5.0 algorithm, or a combination thereof.

8. The method of claim 1 wherein the drug provider includes a doctor, a nurse, a medical provider, a caregiver, an anesthesia provider, a medical specialist, a medical trainee, a patient, a veterinarian, a veterinary technician, or a medical device; and/or
   wherein the computing platform includes a mobile device, a smartphone, a tablet computer, a laptop computer, a computer, a server, or a medical device.

9. The method of claim 1 wherein the drug provider information includes a drug provider identifier, a drug provider job role, and/or a drug provider employment status, wherein the procedure information includes a medical record number, a procedure type, a drug type or class, a drug name, drug equivalency information, a drug dosage, mitigating effects information, and/or a procedure duration, and wherein the patient information includes a patient age, a body weight, a patient discharge disposition, a pain score for the patient, patient medications, and/or a patient physical status; and/or
   wherein at least some of the drug dispensation event data is obtained from a drug dispensing database, an electronic health record medical database, or a database containing information obtained from multiple disparate data management systems.

10. A system using machine learning in detecting drug diversion, the system comprising:
   at least one processor;
   a memory; and
   a computing platform including the at least one processor and the memory, wherein the computing platform is configured for:
      receiving, as input, an observed drug dispensation amount associated with a drug dispensation event related to a drug provider along with other drug dispensation event data, wherein the drug dispensation event data comprises drug provider information, procedure information, and patient information;
      generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm including a neural network trained using one or more data sets associated with historical drug dispensation events including a data set indicating dispensation events and corresponding drug dispensation amounts for the dispensation events; and
      outputting, by the drug diversion detection algorithm, information indicating that the observed drug dispensation amount is aberrant.

11. The system of claim 10 wherein the computing platform is further configured for:
   generating, using information about historical drug dispensation events associated with the drug provider and a drug or class of drugs, a drug dispensation pattern over time associated with the drug provider;
   detecting, using the drug diversion detection algorithm and the drug dispensation pattern, whether the drug dispensation pattern is consistent with drug diversion; and
   outputting, by the drug diversion detection algorithm, information indicating that the drug dispensation pattern is consistent with drug diversion by the drug provider.

12. The system of claim 11 wherein the computing platform is further configured for:
   notifying a user or a related system for administering to the drug provider an intervention.

13. The system of claim 11 wherein the computing platform is configured for detecting that the drug dispensation pattern is consistent with drug diversion by determining that a frequency of aberrant events is increasing and/or by determining that magnitudes of detected aberrancy are increasing over a period of time.

14. The system of claim 11 wherein the computing platform is configured for:
   classifying, using the drug diversion detection algorithm, the drug dispensation pattern over time associated with the drug provider and drug dispensation patterns associated with other drug providers into different drug dispensation groups; and
   notifying a user or a related system about one or more drug dispensation groups or one or more drug providers thereof if a predefined threshold value indicating drug diversion is reached or exceeded.

15. The system of claim 10 wherein the computing platform is configured for training the drug diversion detection algorithm by:
   generating, using the one or more data sets, output data from two or more machine learning algorithms;
   generating, using an ensemble algorithm, ensemble data based on the output data; and
   configuring the drug diversion detection algorithm based on the ensemble data.

16. The system of claim 10 wherein the at least one machine learning algorithm includes a convolutional neural network (CNN), a gradient tree boosting algorithm, a random forest algorithm, a support vector machine algorithm, a penalized logistic regression algorithm, a C5.0 algorithm, or a combination thereof.

17. The system of claim 10 wherein the drug provider includes a doctor, a nurse, a medical provider, a caregiver, an anesthesia provider, a medical specialist, a medical trainee, a patient, a veterinarian, a veterinary technician, or a medical device; and/or
   wherein the computing platform includes a mobile device, a smartphone, a tablet computer, a laptop computer, a computer, a server, or a medical device.

18. The system of claim 10 wherein the drug provider information includes a drug provider identifier, a drug provider job role, and/or a drug provider employment status, wherein the procedure information includes a medical record number, a procedure type, a drug type or class, a drug name, drug equivalency information, a drug dosage, mitigating effects information, and/or a procedure duration, and wherein the patient information includes a patient age, a body weight, a patient discharge disposition, a pain score for the patient, patient medications, and/or a patient physical status; and/or
   wherein at least some of the drug dispensation event data is obtained from a drug dispensing database, an electronic health record medical database, or a database containing information obtained from multiple disparate data management systems.

19. A non-transitory computer readable medium comprising computer executable instructions that when executed by at least one processor of a computer cause the computer to perform steps comprising:
   receiving, as input, an observed drug dispensation amount associated with a drug dispensation event related to a drug provider along with other drug dispensation event data, wherein the drug dispensation event data comprises drug provider information, procedure information, and patient information;
   generating, using a trained drug diversion detection algorithm and the drug dispensation event data, an expected drug dispensation amount associated with the drug dispensation event and determining, using the observed drug dispensation amount and the expected drug dispensation amount, whether the observed drug dispensation amount is aberrant, wherein the drug diversion detection algorithm includes at least one machine learning algorithm including a neural network trained using one or more data sets associated with historical drug dispensation events including a data set indicating dispensation events and corresponding drug dispensation amounts for the dispensation events; and
   outputting, by the drug diversion detection algorithm, information indicating that the observed drug dispensation amount is aberrant.

20. The non-transitory computer readable medium of claim 19 comprising additional computer executable instructions that when executed by the at least one processor of the computer cause the computer to perform steps comprising:

generating, using information about historical drug dispensation events associated with the drug provider and a drug or class of drugs, a drug dispensation pattern over time associated with the drug provider;

detecting, using the drug diversion detection algorithm and the drug dispensation pattern, whether the drug dispensation pattern is consistent with drug diversion; and outputting, by the drug diversion detection algorithm, information indicating that the drug dispensation pattern is consistent with drug diversion by the drug provider.

* * * * *